United States Patent [19]

Kamada et al.

[11] Patent Number: 6,150,149
[45] Date of Patent: Nov. 21, 2000

[54] BASIDIOMYCETE FUNGUS-DERIVED CYTOCHROME P450 GENES

[75] Inventors: Takashi Kamada, Okayama; Hajime Muraguchi, Akita, both of Japan

[73] Assignee: Sumitomo Chemical Company, Limited, Osaka, Japan

[21] Appl. No.: 09/299,662

[22] Filed: Apr. 27, 1999

[30] Foreign Application Priority Data

Nov. 17, 1998 [JP] Japan .................................. 10-327139

[51] Int. Cl.⁷ .............................. C12N 9/02; C12N 1/21; C12N 15/53
[52] U.S. Cl. ...................... 435/189; 435/183; 435/252.3; 435/320.1; 536/23.2
[58] Field of Search ................................. 435/252.3, 183, 435/189, 320.1; 536/23.2

[56] References Cited

PUBLICATIONS

Maraguchi et al., GenBank accession No. 074643, dated Apr. 1998.

*Primary Examiner*—Rebecca E. Prouty
*Assistant Examiner*—Manjunath Rao
*Attorney, Agent, or Firm*—Sughrue, Mion, Zinn, Macpeak & Seas, PLLC

[57] ABSTRACT

The present invention provides:
1. A basidiomycete fungus-derived cytochrome P450 gene;
2. A vector comprising the cytochrome P450 of 1;
3. A transformant which is characterized in that the cytochrome P450 gene of 1 is introduced in a host cell;
4. A method for producing a cytochrome P450 comprising the steps of:
   incubating the transformant of 3; and the like.

10 Claims, 3 Drawing Sheets

```
                              MEMBRANE SPANNING REGION                                                OMURA HINGE
Coprinus cinereus       1  MTTTSSSIFAGIGCL--IVASITYFRKIKANPARAHLPPGKPIPVLGNVKIDLRA---KEL-WLPAMDWAKQ---YGDITM    71
Aspergillus parasiticus 1  M------IYSIIIQAGALLGFLILQKLIAPKDTRPPLPPGPWRKPIIGNLTDFPP---KGTPEWLF--WAKHHERYGPMS    69
Aspergillus flavus      1  M------IYSIIIQAGALIGLMWLEKLIAPKDTRPPLPPGPWRKPIIGNLTDFPP---KGTPEWLF--WAKHQERYGPMS    69
Sorghum bicolor         1  MDA----SLFLSVALAVVLIPLSLALLNRLRLGRLPPGPRPWPVLGNLRQIKPIRCRCFQEW-----AERYGPVI       66
Glycine max             1  M------AILLIIPISLVTLWLGYTLYQRLRF-KLPPGPRPMPVVGNLYIIKPVRFRCFAEW-----AQSYGPII       63

Coprinus cinereus       72 YLHVFGQGLTFIINSLESASDLIEKRGGMYADKPQFTMVCELCNCKNMVAFTPYGEQSKRQRRIMKAFAPAR-IPDYHPLM  151
Aspergillus parasiticus 70 SLFVMGQTIIMINDAHLGIEIMHKKSALSQMIPD-APFAHMAGWGMSLATERNKQAWKTIRANMKQEIGTRRAIATFHPKM  149
Aspergillus flavus      70 SLFVMGQTIIMINDAHLGIEIMHKKSALSQMIPD-APFAHMAGWGMSLATERNKQAWKTIRANMKQEIGTRRAISTFHPKM  149
Sorghum bicolor         67 SVWFGSGLTVVSTSELAKEVLKENDQQIADRPNRSTQRFSRNGQDLIWADYGPHYIKVRKLCNLELFTPKRLEALRPIR    147
Glycine max             64 SVWFGSTLNIVSNSELAKEVLKEHDQLLADRHRSRSAAKFSRDGKDLIWADYGPHYVKVRKVCTLELFSPKRLEALRPIR   144

Coprinus cinereus      152 ESSTNLFLRNV-------IASPADYIGHVRRYSGSLTLNIVGYEVTSNEDEYIM-MAFECVGILANEIASAGVWAVD     222
Aspergillus parasiticus 150 EIGRRFLRT---------LDNPDDLRFHIRKEANAFMDVAYGYTIAPHGKDELYDLTQQSVRQFSHIFSP--GEMSVN    219
Aspergillus flavus     150 EIGRRFLRT---------LDNPDDLRFHIRKEANAFMDVAYGYTIAPHGKDELYDLTQQSVRQFSHIFSP--GEMSVN    219
Sorghum bicolor        148 EDEVTAMVESVYRAATAPGNEGKPMVVRNHLSMVAFNNITRLAFGKRFM-NANGDIDEQGREFKTIVNNGIKIGASLSVAE  227
Glycine max            145 EDEVTSMVDSVYNHCTSTENLGKGILLRKHLGVVAFNNITRLAFGKRFV-NSEGVMDEQGVEFKALVENGLKLGASLAMAE  224

Coprinus cinereus      223 VMPFLAKIPKWAEGLPGMSFKRKARKMWKKMMEDWVDGPFEYVKNTMKSGTYKQSFCSSLLDDESISQTQEHFEFDLKWTAN 303
Aspergillus parasiticus 220 FFPILRYVPSW---FPGASFQIKAAEYKRTIERMTMVPYLWIKDQVARGCTRPSILLRLLQKGHY-ESGSHQEQVLWTNA   296
Aspergillus flavus     220 FFPILRYVPSW---FPGASFQIKAAEYKRTIERMTMVPYLWIKDQVARGCSRPSILLRLLQKGHY-ESGSHQEQVLWTNA   296
Sorghum bicolor        228 FI---WYL-RWLCPLNEELYKTHNERRDRLTMKIIEEH---AKSLKESG-AKQHFVDALFTLKQQYDLSEDTIVIGLLW--  297
Glycine max            225 HID--W-L-RWMFPLEEGAHAKHGARRDRLTRAIMAEH---TEARKKSGGAKQHFVDALITLQDKYDLSEDTIIGLLW--  295
```

BASIDIOMYCETE FUNGUS-DERIVED CYTOCHROME P450 GENES

BACKGROUND OF THE INVENTION

1. Field of the Invention

The present invention relates to a basidiomycete fungus-derived cytochrome P450 gene.

2. Description of the Related Art

A cytochrome P450 is a proto hem-containing protein exhibiting a Soret band around 450 nm upon binding in a reduced form with carbon monoxide, and generally occurs in a variety of molecular species, which are involved in oxidation, peroxidation and reductive metabolism of various endogenous substances. A cytochrome P450 is involved not only in the metabolism of endogenous substances but also in the metabolism of exogenous substances such as pharmaceuticals, environmental chemicals, naturally-occurring plant products, alcohols and the like. For example, in a plant, several species of cytochrome P450 are involved in the biosynthesis of phytohormones relating to the differentiation and the development of a plant, such as gibberellin and brassinolide. The structure of such cytochrome P450 gene in an animal or a plant as well as an ascomycete fungus are known but that in a basidiomycete fungus has not been characterized at all.

On the other hand, a recent advance in a gene recombination technology promotes an attempt, in the field of a breeding technology of agricultural and horticultural plants, to produce a novel plant which is transformed advantageously by means of introducing a gene capable of expressing some advantageous characteristics into a plant.

SUMMARY OF THE INVENTION

An objective of the present invention is to provide a gene capable of being utilized in the breeding technology of basidiomycetes fungi and plants.

Under the aformentioned circumstances, the present inventors studied hard and then discovered a cytochrome P450 gene in *Coprinus cinereus* which is a basidiomycete fungus, which resulted in completion of the present invention.

The present invention provides:

1. A basidiomycete fungus-derived cytochrome P450 gene.
2. A gene encoding a basidiomycete fungus-derived cytochrome P450 whose homology with the entire amino acid sequence of a cytochrome P450 classified in CYP 64 family is 50% or less.
3. The gene described above in 2 wherein the homology with the nucleotide sequence corresponding to the entire amino acid sequence of a cytochrome P450 classified in CYP 64 family is 40% or less.
4. A gene encoding the following protein (a), (b) or (c):
   (a) a cytochrome P450 having the amino acid sequence shown by SEQ ID: No.1.
   (b) a cytochrome P450 having the amino acid sequence shown by SEQ ID: No.4.
   (c) a cytochrome P450 having an amino acid sequence in which one or several amino acids are deleted, substituted, modified or added in the amino acid sequence shown by shown by SEQ ID: No.1.
5. A cytochrome P450 gene having the nucleotide sequence shown by SEQ ID: No.2.
6. A cytochrome P450 gene having the nucleotide sequence shown by SEQ ID: No.3.
7. A cytochrome P450 gene having the nucleotide sequence shown by SEQ ID: No.5.
8. A cytochrome P450 gene having the nucleotide sequence shown by SEQ ID: No.6.
9. A vector comprising the cytochrome P450 gene of any one of 1 to 8.
10. A transformant which is characterized in that the cytochrome P450 gene of any one of 1 to 8 is introduced in a host cell.
11. A transformant which is characterized in that the vector of claim 9 is introduced in a host cell.
12. A method for producing a cytochrome P450 comprising the step of:
    incubating the transformant of 10 or 11; and
    allowing said transformant to produce a cytochrome P450.
13. A cytochrome P450 produced by the method of 12.
14. A cytochrome P450 having the amino acid sequence shown by SEQ ID:. No.1 or No.4.
15. A cytochrome P450 having an amino acid sequence in which one or several amino acids are deleted, substituted, modified or added in the amino acid sequence shown by SEQ ID: No.1.

Figure 1:
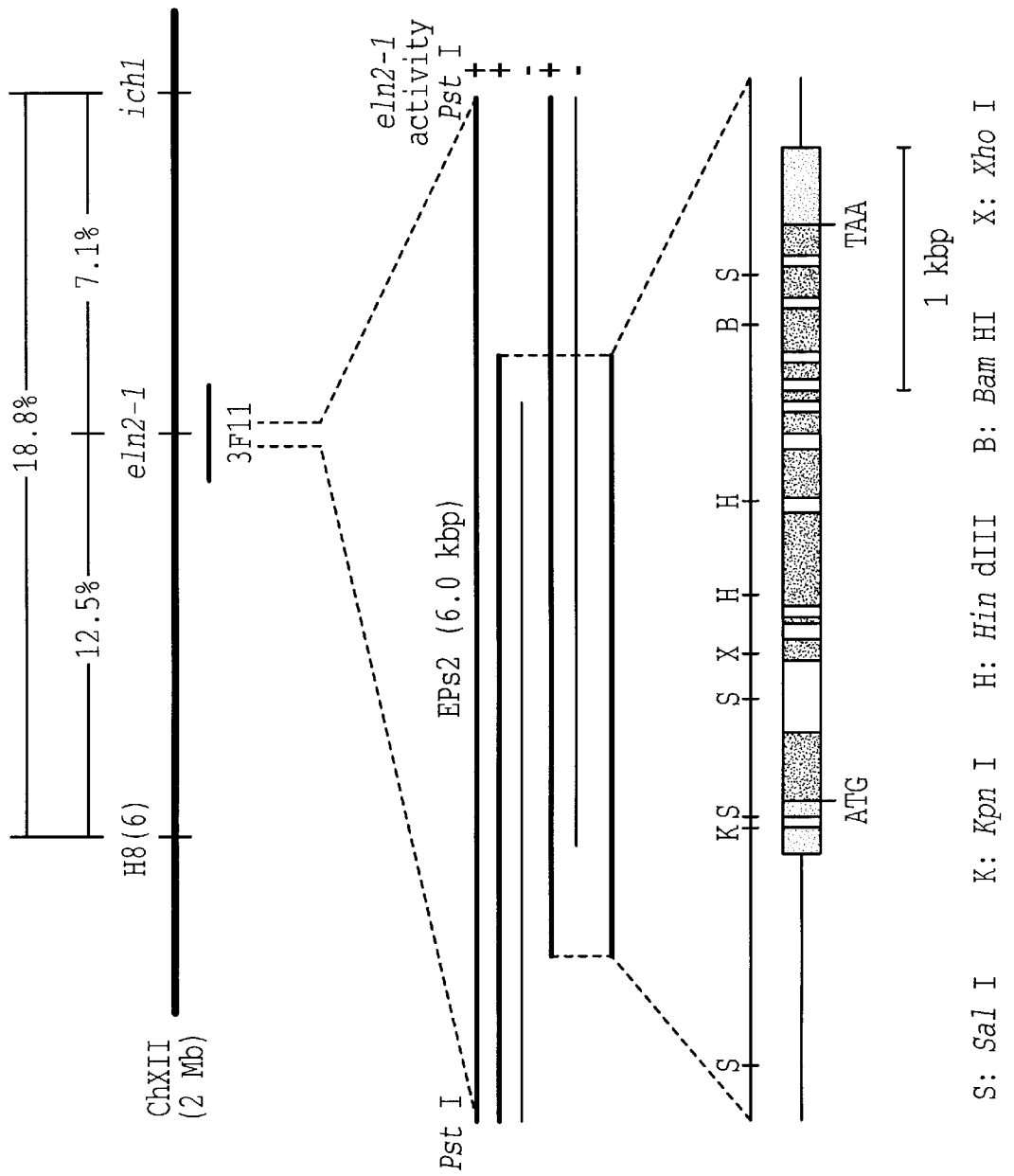
FIG. 1 shows a gene map of a cytochrome P450 gene eln2 in the present invention.

The top figure represents the location of the eln2-1 variation on chromosome XII (ChXII), and the distance to ich1 locus or to RFLP marker H8(6) is represented as a ratio of recombination (%). The region cloned to a cosmid clone 3F11 is represented as a bar.

The middle figure shows a cosmid clone 3F11-derived 6.0 kb PstI fragment and the DNA fragment obtained by introducing a deletion into the former together with the eln2-1 variation activities of the both.

The bottom figure shows the restriction enzyme map of wild type eln2 gene. A solid square represents an exon, an open square represents an intoron, and a hatched square represents 5'- or 3'-non-coding region. ATG is an initiation codon and TAA is a stop codon.

Figure 2B:
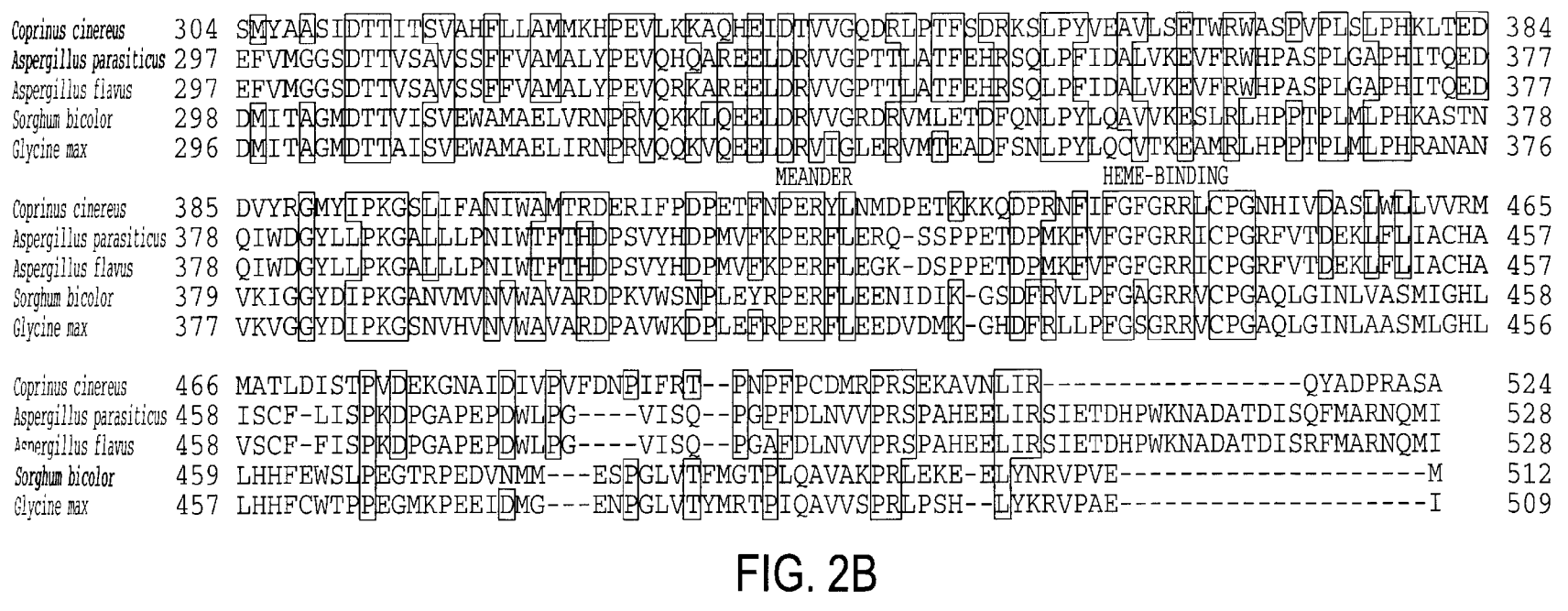

FIG. 2 shows the amino acid sequence of a cytochrome P450 Eln2 of the present invention in comparison with that of other cytochrome P450s. An amino acid is represented as one letter and an amino acid in agreement with the amino acid of a cytochrome P450 Eln2 in the present invention is indicated in a square. The amino acid sequences shown are those of a cytochrome P450 Eln 2 in the present invention, *Aspergillus parasiticus*-derived P450, *Aspergillus flavus*-derived P450, *Sorghum bicolor*-derived P450, and *Glycine max*-derived P450, in this order from the top to the bottom.

DESCRIPTION OF THE PREFERRED EMBODIMENT

The present invention will be described in detail.

A cytochrome P450 gene in the present invention can be obtained from Eubasidiomycetes which typically relate or pertain to Agaricales, more specifically, basidiomycete fungus, such as a *Coprinus cinereus,* according to the gene engineering procedure described by J. Sambrook, E. F. Frisch, T. Maniatis (Molecular Cloning 2nd edition, published by Cold Spring Harbor Laboratory, 1989). First, a genome DNA library is prepared, for example, from *Coprinus cinereus.* After extracting a genome DNA from *Copri-* nus cinereus followed by digestion with a restriction enzyme, the DNA fragments are fractionated according to a known procedure such as a sucrose density gradient centrifugation or a cesium chloride equilibrated centrifugation. In such procedure, a particular chromosome may previously be separated by means of a pulse electrophoresis and the like. Each of the DNA fragments thus obtained is ligated to a vector, such as a commercial plasmid, phage or cosmid to prepare a genome DNA library. Using this genome DNA library, a genome gene encoding a cytochrome P450 in the present invention can be obtained by means of a hybridization method employing the DNA fragment having a partial nucleotide sequence of the nucleotide sequence shown by SEQ ID: No.2 as a probe, or a PCR method employing an oligonucleotide having a partial nucleotide sequence of the nucleotide sequence shown by SEQ ID: No.2 as a primer. A primer employed in such PCR method may be obtained, for example, by selecting a nucleotide sequence having a 20 bp to 40 bp length and whose a ration of G and C base is 40% to 60% from each of the 5'-non-coding region and 3'-non-coding region of the nucleotide sequence shown by SEQ ID: No.2 followed by synthesizing an oligonucleotide having such nucleotide sequence. More particularly, the nucleotide sequence of a forward primer may for example be 5'-GGCGAGATGGGTGTTTATGAGACTGG-3' and the nucleotide sequence of a reverse primer may for example be 5'-CGGTGTTTCGAGGCGTTTCTGGTTGA-3'. A gene in the present invention which has been amplified by a PCR method may for example be cloned to a vector according to a gene engineering procedure described by J. Sambrook, E. F. Frisch, T. Maniatis (Molecular Cloning 2nd edition, published by Cold Spring Harbor Laboratory, 1989). More particularly, the cloning may for example be conducted using TA cloning kit (Invitrogen) or a commercial plasmid vector such as pBluescriptII (Stratagene). The nucleotide sequence of a DNA fragment thus cloned may for example be identified according to the dye deoxyterminating method described by F. Sanger, S. Nicklen, A. R. Coulson (Proceedings of National Academy of Science, USA (1977), 74, p5463–5467). For example, a commercial kit such as ABI PRISM Dye Terminator Cycle Sequencing Ready Reaction Kit manufactured by Perkin Elmer may be employed.

In addition, from a basidiomycete fungus classified to an order of Agaricales such as *Coprinus cinereus,* a cDNA gene encoding a cytochrome P450 in the present invention may be prepared. First, an RNA is prepared from a basidiomycete fungus classified to an order of Agaricales such as *Coprinus cinereus.* More particularly, a pileus of *Coprinus cinereus* is pulverized in a solution containing a potent protein denaturing agent such as guanidine hydrochloride or guanidine thiocyanate and then the pulverized material is treated with phenol or chlroform, whereby denaturing the protein. The denatured protein thus obtained is removed for example by a centrifugation, and then from the soluble fraction thus recovered an entire RNA is extracted by means of a guanidine hydrochloride/phenol method, an SDS-phenol method, a guanidine thiocyanate/CsCl method and the like. As a commercial RNA preparation kit applicable to these methods, ISOGEN (NIPPON GENE) may be exemplified. The RNA extract thus obtained was subjected to an ethanol precipitation to recover the RNA, from which an RNA having a poly-A chain is fractionated by a conventional method. In such fractionation procedure, a commercial apparatus such as Oligo dT column may be used. From the RNA having a poly-A chain thus obtained, a cDNA is synthesized by a conventional method. In such synthetic procedure, a commercial cDNA synthesis kit may be used. Subsequently, a primer having a partial nucleotide sequence of the nucleotide sequence shown by SEQ ID: No.3 (3'-downstream region-amplifying primer) and a primer having the nucleotide sequence complementary to the nucleotide sequence shown by SEQ ID: No.3 (5'-upstream region-amplifying primer) are prepared. Such 5'-upstream region-amplifying primer may preferably be designed based on the nucleotide sequence located 3'-downstream of the nucleotide sequence selected as a 3'-downstream region-amplifying primer, and more particularly, the nucleotide sequence of a 3'-downstream region-amplifying primer may for example be 5'-TTTACGCCCTACGGAGAACAGTCGAAG-3' and the nucleotide sequence of 5'-upstream region-amplifying primer may for example be 5'-CGGAGGAAGAGGTTGGTTGATGATTCC-3'. Then, using as a template a DNA fragment having an adapter DNA attached at the terminal of a *Coprinus cinereus*-derived cDNA or a DNA of a vector into which *Coprinus cinereus*-derived cDNA fragment has been inserted, a primer having a partial nucleotide sequence of the adapter DNA or a primer having a partial nucleotide sequence of the vector DNA is used in combination with the 5'-upstream region-amplifying primer described above to perform a polymerase chain reaction, whereby amplifying the DNA fragment (5' RACE method). On the other hand, a primer having a partial nucleotide sequence of the adapter DNA or a primer having a partial nucleotide sequence of the vector DNA is used in combination with the 3'-downstream region-amplifying primer to perform a polymerase chain reaction similarly, whereby amplifying the DNA fragment (3' RACE method). A DNA fragment having an adapter DNA attached at the terminal of a *Coprinus cinereus*-derived cDNA used here as a template may for example be obtained by attaching a polymer of a base such as cytosine as an adapter DNA using a terminal deoxynucleotidyl transferase to a *Coprinus cinereus*-derived cDNA prepared as described above, or attaching an adapter of a commercial RACE (rapid amplification of cDNA ends) reaction kit such as the adapter included in Marathon cDNA amplification kit (Clontech) to a *Coprinus cinereus*-derived cDNA. As a primer having a partial nucleotide sequence of an adapter DNA, a primer specific to an adapter included in a commercial RACE reaction kit, such as AP-1 primer or AP-2 primer included in Marathon cDNA amplification kit (Clontech), may be exemplified. As a primer having a partial nucleotide sequence of the vector DNA, for example in the case where the vector is a λ phage-derived vector, a primer specific to the arm region of the λ phage such as λ gt11 reverse primer or λ gt11 forward primer may be employed.

Each of the two DNA fragments amplified as described above is then cloned to a plasmid whereby determining its nucleotide sequence. The overlapped region in the nucleotide sequences thus determined is overlaid on each other, and such nucleotide sequences are ligated with each other to form one nucleotide sequence. Based on the information on the nucleotide sequence thus determined, a primer containing the nucleotide sequence near the translation initiation codon of the nucleotide sequence of a cDNA gene encoding a cytochrome P450 of the present invention (N-terminal primer) and a primer containing the nucleotide sequence complementary to the nucleotide sequence near the stop codon (C-terminal primer) are prepared, and then a polymerase chain reaction is performed using as a template a *Coprinus cinereus*-derived cDNA and also using the both terminal primers described above to amplify the DNA containing the entire length of the cDNA gene encoding a cytochrome P450 in the present invention, whereby accomplishing the cloning. A cDNA gene encoding a cytochrome P450 in the present invention may be obtained also by ligating the DNA fragments obtained in the cDNA gene obtaining process described above at the restriction enzyme recognition sites located in the overlapped region.

A cDNA gene encoding a cytochrome P450 in the present invention may be obtained also by a hybridization method. For example, a *Coprinus cinereus*-derived cDNA prepared as described above is inserted into a vector to prepare a cDNA library, from which a clone of cDNA gene encoding a cytochrome P450 of the invention is selected by means of a hybridization method using as a probe a DNA fragment having a partial nucleotide sequence of the nucleotide sequence shown by SEQ ID: No.3. Thus, the cytochrome P450 in the present invention can be obtained. An example of the conditions for the hybridization is described below. For example, a DNA fragment having a partial nucleotide sequence of the nucleotide sequence shown by SEQ ID: No.3 is radiolabeled using a commercial radiolabeling kit (for example, Random Primer DNA Labeling Kit Ver.2 (Takara)) to prepare a probe DNA. *E. coli* having a plasmid DNA included in the library of a *Coprinus cinereus*-derived cDNA is incubated for 10 hours on an LB medium plate and transferred onto a commercial nylon membrane (for example, Hybond™-N$^+$, Amersham Life Science), which is subjected to the treatment with 10% SDS for 3 minutes, followed by an alkaline denaturing solution (0.5M NaOH, 1.5M NaCl) for 5 minutes followed by a neutralization solution (0.5M Tris-Cl, pH7.0, 1.5M NaCl) for 3 minutes followed finally by 2×SSPE (20 mM phosphate buffer, pH7.4, 0.3M NaCl, 5 mM EDTA) for 3 minutes, which is repeated twice, and then dried and irradiated with an ultraviolet for 3 minutes to immobilize the DNA on the membrane. A pre-hybridization is performed at 65° C. for 1 hour in a pre-hybridization solution (5×Denhart's solution, 5×SSPE, 0.1% SDS, 100 μg/ml denatured salmon testicular DNA), and then a hybridization is performed at 65° C. for 12 hours in a hybridization solution (5×Denhart's solution, 5×SSPE, 0.1% SDS) supplemented with a radiolabeled probe. Thereafter, the membrane is washed twice with 6×SSP at 65° C. for 10 minutes followed by 2×SSP containing 0.1% SDS at 42° C. for 10 minutes, and then an X ray film is exposed to the membrane, whereby detecting a positive colony.

A cytochrome P450 gene in the present invention which can be obtained as described above includes a gene encoding a basidiomycete fungus-derived cytochrome P450 whose homology with the entire amino acid sequence of a cytochrome P450 classified in CYP 64 family is about 40% or less, an above-mentioned gene whose homology with the nucleotide sequence corresponding to the entire amino acid sequence of a cytochrome P450 classified in CYP 64 family is about 40% or less, and the like.

A cytochrome P450 constitutes a gene superfamily, and characterized and designated based on the analogy in the amino acid sequence. Initially the amino acid sequence homology of 40% or higher was required for an identical family, and the homology of 55% or higher was required for an identical subfamily. According to Nelson et al (Pharmacogenetics, 6, 1–42 (1996)), 481 kinds of cytochrome P450 genes and 22 kinds of pseudo-genes had been sequenced at the time point of Oct. 18, 1995, and were classified into 74 kinds of gene families. When a novel cytochrome P450 sequence is identified, the sequence is designated upon sending the information on the sequence to the committee organized by Nelson et al with reference to the sequence data. A cytochrome P450 gene in the present invention was classified in a novel cytochrome P450 family because of its 31% amino acid homology with the closest CYP 64 (Refer to Example 3), and was designated as CYP502.

A cytochrome P450 gene in the present invention may also be a gene encoding a cytochrome P450 having the amino acid sequence shown by SEQ ID: No.1, a gene encoding a cytochrome P450 having the amino acid sequence shown by SEQ ID: No.4, and a gene encoding a cytochrome P450 having an amino acid sequence in which one or several amino acids are deleted, substituted, modified or added in the amino acid sequence shown by shown by SEQ ID: No.1, and those mentioned more particularly is a cytochrome P450 gene having the nucleotide sequence shown by SEQ ID: No.2 or 5 which can be obtained from a *Coprinus cinereus*-derived genome DNA, a cytochrome P450 gene having the nucleotide sequence shown by SEQ ID: No.3 or 6 which can be obtained from a *Coprinus cinereus*-derived cDNA and the like. The deletion, the substituent, the modification, or the addition of one or several amino acids described above includes a polymorphic variation occurring naturally such as a variation in an amino acid sequence associated with the difference in species of basidiomycete fungi, cell line, individual, organ and tissues, as well as a variation induced artificially by subjecting a basidiomycete fungus to a mutating treatment. The expression "several" amino acids means 2 to 40 amino acids, preferably 2 to 20 amino acids. Such cytochrome P450 gene in the present invention may be a naturally-occurring gene or a gene produced by introducing a variation into a naturally-occurring gene by means of a gene engineering procedure such as a site-specific variation introducing method or a random variation introducing method.

A cytochrome P450 gene in the present invention prepared as described above can be integrated, by means of an conventional gene engineering procedure, into a vector capable of being used in a host cell to be transformed, such as a vector which contains a gene information capable of being replicated in a host cell, which can proliferate independently, which can readily be isolated and purified from the host cell, and which has a detectable maker, whereby constructing a vector containing a cytochrome P450 gene in the present invention (hereinafter referred to as the present vector). In this procedure, a promoter capable of functioning in a host cell, a cytochrome P450 gene in the present invention and a terminator capable of functioning in a host cell are bound in a functional form in this order, whereby constructing an expression plasmid capable of expressing a cytochrome P450 gene of the invention in a host cell. The expression "bound in a functional form" means that a cytochrome P450 gene in the present invention is bound to a promoter in such a condition that it can be expressed under the regulation by said promoter in a host cell to which it is to be introduced.

A promoter capable of functioning in a host cell includes a lacZ gene promoter of a lactose operon of *E. coli*, an alcohol dehydrogenase gene (ADH) promoter of a yeast, an adenovirus major late (Ad.ML) promoter, SV 40 early promoter and a vaculovirus promoter and the like. A promoter capable of functioning in a plant cell includes a T-DNA-derived constitutive promoter such as a noparin synthetase gene (NOS) promoter, an octopine synthetase gene (OCS) promoter and the like, a plant virus-derived promoter such as a cauliflower mosaic virus (CaMV)-derived 19S and 35 S promoters, an inducing promoter such as phenylalanine ammonia lyase (PAL) gene promoter, a chalcone synthase (CHS) gene promoter, a pathogenesis-related protein (PR) gene promoter and the like. In addition to those listed above, any known plant promoter may also be employed.

A terminator capable of functioning in a host cell include an HIS terminator sequence of a yeast, an ADH1 terminator, an early splicing region of SV40 and the like. When a host cell is a plant, a terminator capable of functioning in a plant cell includes a T-DNA-derived constitutive terminator such as a noparin synthetase gene (NOS) terminator, a plant virus-derived terminator such as a terminator of garlic viruses GV1 and GV2, and the like.

A method for transforming a host cell by the present vector thus constructed may be any conventional methods suitable to the host cell transformed, and, when a microorganism E. coli is employed as a host cell, a calcium chloride method or an electroporation method described by J. Sambrook, E. F. Frisch, T. Maniatis (Molecular Cloning 2nd edition, published by Cold Spring Harbor Laboratory, 1989) may be employed. When a yeast is employed as a host cell, the present vector may be introduced according to, for example, a lithium method. When a host cell is a plant, then the present vector may be introduced into the plant cell by a known procedure employing an agrobacterium infection (Japanese Patent Applications Laid-Open 2-58917 and 60-70080), an electroporation into a protoplast (Japanese Patent Applications Laid-Open 60-251887 and 5-68575), or a particle gun (Japanese Patent Applications Laid-Open 5-508316 and 63-258525) and the like, and then a plant cell to which a cytochrome P450 gene in the present invention has been introduced is selected to obtain a transformed plant cell. The transformed plant cell may be subjected to a conventional plant cell culture such as that described by H.UCHIMIYA (PLANT GENE ENGINEERING MANUAL, METHOD FOR PRODUCING TRANSGENIC PLANT, 1990, KODANSHA, SCIENTIFIC (ISBN4-06-153515-7, C3045, p.27 to 55)) to regenerate the plant body, whereby obtaining a transformed plant body. For the purpose of selecting a transformant, a method based on the nature of a selecting marker possessed by the present vector may for example be employed.

A transformant thus obtained, into which a cytochrome P450 gene in the present invention has been introduced, is cultured to allow the cytochrome P450 in the present such as a cytochrome P450 having the amino acid sequence shown by SEQ ID: No.1 or No.4, a cytochrome P450 having an amino acid sequence in which one or several amino acids are deleted, substituted, modified or added in the amino acid sequence shown by shown by SEQ ID: No.1 to be produced.

For example, when a transformant is a microorganism, then the transformant can be cultured in any medium employed in a conventional culture of a general microorganism which contains appropriate carbon sources, nitrogen sources, organic and inorganic salts and the like. The carbon sources may be glucose, glycerol, dextrin, sucrose, organic acids, animal and vegetable oils, molasses and the like. The nitrogen sources may be organic and inorganic nitrogen sources such as meat extracts, peptone, yeast extracts, malt extracts, soybean flakes, corn steep liquor, cottonseed flakes, dry yeasts, casamino acid, sodium nitrate, urea and the like. The organic and inorganic salts may be chlorides, sulfate, acetates, carbonates and phosphates of potassium, sodium, magnesium, iron, manganese, cobalt, zinc and the like, such as sodium chloride, potassium chloride, magnesium sulfate, ferrous sulfate, manganese sulfate, cobalt chloride, zinc sulfate, cupric sulfate, sodium acetate, calcium carbonate, sodium carbonate, potassium hydrogen phosphate, dipotassium hydrogen phosphate and the like. The culture may be conducted by a conventional method in a general microorganism such as a solid culture and a liquid culture (culture tube shaking, reciprocal shaking, jar fermenter, tank fermentation and the like). Especially when a jar fermenter is employed, an aseptic air should be supplied and an air in a volume usually about 0.1 to 2 times/minute that the culture medium should be supplied. The culture temperature may vary within the range allowing a microbial growth, and the culture medium is kept preferably at a temperature of about 15° C. to about 40° C. and at a pH of about 6 to about 8. The culture is continued for a period varying depending on various factors of the culture condition, and usually continued for a period of about I to 5 days.

A cytochrome P450 in the present invention produced by a transformant may be recovered by a combination of appropriate and conventional isolation and purification methods, and, for example, the transformant, after completion of the culture, is collected by centrifugation and pelletized or lysed and then an intended enzyme can be isolated and purified by a combination of various chromatographic methods such as ion exchange, hydrophobic, gel filtration, affinity-based procedures. A fraction containing a cytochrome P450 in the present invention can be selected using as an index a cytochrome P450-specific absorption observed at 450 nm in a reduced CO bond-differentiated spectrum.

A cytochrome P450 gene having the nucleotide sequence encoding the amino acid sequence shown by SEQ ID: No.4 reduces the length of the stipe of the fruit body of a basidiomycete fungus.

EXAMPLES

The present invention is further detailed in the following examples, which are not intended to restrict the present invention.

Example 1

Isolation and characterization of eln2-1 variant

C. cinereus strains 5401 (A1B1) and 5302 (A2B2) were homokaryon of a wild type used as a standard strain in the inventors' laboratory, and C. cinereus strain CopD5–12 (A12B12) was a field-sampled, fruit body-derived basidiospore. The oidium of strain CopD5–12 was UV-treated, and variant Uad605 having a fruit body mutation [elongationless 2-1 (eln2-1)] observed as a short stipe was obtained. This variant underwent no elongation of the stipe at the fruit body maturing stage, and its stipe was kept short and the basal part of its fruit body was broken. While a wild type undergoes the formation of the primordial axis at the initial stage of the fruiting to form a basal part of the primordium of the fruit body, the variant obtained here exhibited a retarded development of the primordial axis when comparing with the pileus tissues, resulting in a primordium having a large number of the pileus tissues. In addition, the variant had a laterally-swollen primordial axis and appeared in a corpulent and short shape. Accordingly, it was suggested that eln2-1 variation had some effects not only on the elongation of the stipe but also on the development of the primordial axis, resulting in an imbalance of the growth between the primordial axis and the pileus tissues. A section was prepared from a corpulent short primordium of this variant and observed by an optical microscope and it was proven that the primordial axis had a defect in the tissue structure and was winding.

Since a conjugant having this eln2-1 variation heterozygously underwent the formation of a corpulent short primordium, this variation was considered to be dominant. However, the conjugant having the eln2-1 variation heterozygously underwent the formation of a stipe which was just a little longer than that of a conjugant having the eln2-1 variation homozygously. Accordingly, strain C44 (A12B12 eln2-1) which was a progeny between C. cinereus strains Uad605 and 292 (A3B1 trp 1-1, 1-6) was hybridized with strain 5302, and the segregation of the variation eln2-1 into an F1 generation was assessed. As a result, the phenotype was segregated at the ratio of about 1:1 (53:51) in the F1 generation, revealing that the variation eln2-1 was attributable to the variation in the gene on a chromosome, and this gene was designated as eln2.

In addition, C. cinereus strain 292 (A3B 1 trp 1 - 1, 1-6) was obtained from Dr.Pukkila (Department of Biology, University of North Carolina, Chapel Hill).

Subsequently, the linkage of the eln2-1 variation to various chromosomal markers was analyzed in order to determine the location of gene eln2 on the chromosome. As a result, eln2 locus was proven to be linked to ich1-1 locus on chromosome XII at a ratio of the recombination rate of 7.1%. The linkage of eln2 locus to H8(6) which is an RFLP marker of chromosome XII was also investigated and the results indicated the linkage at a ratio of the recombination rate of 12.5%, thus proving that eln2-1 locus is mapped on chromosome XII (FIG. 1).

Example 2

Cloning of eln2-1 variation gene of Coprinus cinereus

Since eln2-1 variation was dominant, the transformant obtained by introducing the variation gene into a wild strain must exhibit an eln2-1 variation character. Accordingly, a chromosome XII-specific cosmid library was prepared and transformed into a wild type strain to screen a clone capable of causing an eln2-1 variation character by means of a sibb selection method (sister selection method). The chromosome XII-specific cosmid library was prepared from a back cross variant of strain C44 according to the method by Zolan et al. (Nucleic Acids Res., 20, 3993–3999, 1992). This library consisted of 480 clones (5 96-well plates). The DNAs prepared from 12 clones were pooled, and C. cinereus strain 292 (A3B1 trp1-1, 1-6) was transformed. The trp+ transformant formed on an R medium was picked up and cultured for 2 days in a minimum medium to prepare a mycelium.

In addition, R medium is as follows.

| /500 mL | |
|---|---|
| Asparagine H$_2$O | 1.14 g |
| MgSO$_4$7H$_2$O | 0.06 g |
| Glucose | 2.5 g |
| Sucrose | 85.6 g |
| Dist. Water 430 mL | |
| 40*NCM salts | 12.5 mL |
| 1 mg/mL Thiamine | 0.5 mL |
| Agar | 7.5 g |
| Potato starch | 2.5 g |
| Autoclaved for 15 min | |
| 40*NCM salts: | |
| NH$_4$Cl | 60 g |
| Na$_2$HPO$_4$ 7H$_2$O | 109.6 g |
| KH$_2$PO$_4$ | 54 g |
| Na$_2$PO$_4$ | 11.6 g |
| Dist. Water 1 Liter sterilized by filtration | |

The mycelium was conjugated to strain 5302, and the phenotype of the fruit body formation was observed. As a result, a cosmid clone designated as 3F11 induced the variation eln2-1 character. In addition, a 6.0 kb PstI fragment derived from this clone, upon transforming the wild type strain, induced the eln2-1 character. Accordingly, this DNA fragment was subcloned to pBluescript II SK(+) and the deletions of various lengths were introduced into this DNA fragment from the both terminals using Nested Deletion Kit, and then used to transform the wild type strain, whose phenotype was then analyzed, whereby revealing that the eln2-1 variation activity was on a 4.4 kb DNA fragment (FIG. 1).

Example 3 eln2 gene nucleotide sequencing

The nucleotide sequences of the both chains of the 4.4 kb DNA fragment obtained in Example 2 were determined. Determination of the nucleotide sequences was performed using Perkin Elmer DNA Sequencer Model 373A together with ABI PRISM DNA Sequencing Kit. As a result, the nucleotide sequence shown by SEQ ID: No.5 was obtained, and was converted into an amino acid sequence, whereby obtaining the amino acid sequence shown by SEQ ID: No.4. A cytochrome P450 gene in the present invention having the nucleotide sequence coding the amino acid sequence shown by SEQ ID: No.4 thus characterized has an ability of reducing the stipe of the fruit body of a basidiomycete fungus.

On the other hand, mRNA prepared from a pileus was converted to cDNA using Marathon cDNA Amplification Kit (Clontech). Using this cDNA as a template together with eln2 gene-specific primers (5'-TTTACGCCCTACGGAGAACAGTCGAAG-3', 5'-CGGAGGAAGAGGTTGGTTGATGATTCC-3') and AmpliTaq Gold DNA Polymerase (Perkin Elmer), the DNA was amplified by means of an RACE method. An amplified DNA fragment was cloned using pCR2.1 as a vector, and the nucleotide sequence was determined. As a result, the nucleotide sequence shown by SEQ ID: No.6 was obtained.

Based on the comparison of the nucleotide sequences between a genome DNA-derived gene and a cDNA-derived gene, it was revealed that ORF coded by eln2 gene was interrupted by 11 intorons (FIG. 1). The first intoron was located in a 5'-non-coding region. The second intron was of 300 bp, which was longer than a typical intron of a filamentous fungus.

The amino acid sequence of Eln2 protein coded on eln2 gene thus obtained was compared with a data base. As a result, this protein had a significant sequence homology with a P450 gene superfamily (FIG. 2). Eln2 protein had an N-terminal membrane binding region, oxygen and substrate binding regions, highly conservative hem binding sequence, which are in common with cytochrome P450s, and its secondary configuration was also characteristic to cytochrome P450s. Based on the results of these investigation, Eln2 protein was characterized as a cytochrome P450 of a microsome type. The cytochrome P450 molecular species closest to Eln2 was CYP64 family, which included oxide reductase of Aspergillus parasiticus (Yu et al., Appl. Environm. Microbiol., 63, 1349–1356, 1997) and OMST-oxide reductase of *Aspergillus flavus* (Prieto & Woloshuk, Appl. Environm. Microbiol., 63, 1661–1666, 1997). However, the homology of the amino acid between Eln2 and CYP 64 family was only 31%, and Eln2 was proven to be classified into a novel P450 family.

Example 4 eln2-1 variation site

To determine the eln2-1 variation site, the nucleotide sequence (SEQ ID: No.2) of eln2 gene derived from a genome DNA of a wild type strain CopD5–12 and the nucleotide sequence (SEQ ID: No.3) of eln2 gene derived from cDNA prepared from a wild type strain were determined. More particularly, a pair of the primers (5'-GGCGAGATGGGTGTTTATGAGACTGG-3', 5'-CGGTGTTTCGAGGCGTTTCTGGTTGA-3') was employed to amplify the wild type eln2 gene from the genome DNA of the wild type strain CopD5–12 by means of PCR, and the nucleotide sequence of the resultant PCR product was sequenced using Dye-Terminator Sequencing Kit (Perkin Elmer). The nucleotide sequence of the genome eln2 gene of the wild type strain CopD5–12 thus obtained (SEQ ID: No.2) was compared with the nucleotide sequence of eln2-1 variation gene (SEQ ID: No.5). As a result, the variation gene exhibited the deletion of 4 bases from Base No.3680 to 3683 in SEQ ID: No. 2, which leaded to the appearance of the stop codon tga (Base No.3679 to 3681 in SEQ ID: No.5), which leaded to the deletion of 18 amino acid residues present at the C-terminal of the wild type protein. These findings were supported also by the nucleotide sequence (SEQ ID: No.3) of the cDNA eln2 gene prepared from the wild type strain. Consequently, the eln2-1 variation was proven to be attributable to the deletion of the 4 bases described above.

Example 6

Expression of eln2

In order to investigate whether the expression of eln2 gene is regulated in the process of the development of *Coprinus cinereus,* RNAs were prepared from a vegetative proliferation mycelium, primordium, pileus and stipe of a wild strain and from a primordium of an eln2-1 variation strain, and subjected to the northern analysis using as a probe a 3.0 kb KpnI fragment coding eln2-1 variation gene. As a result, eln2 gene was proven to give a transcription product of about 2.5 kb, and was expressed constitutively in both strains.

Advantage

The present invention provides a gene capable of being utilized in the breeding technology of basidiomycete fungi and plants.

What is claimed is:

1. An isolated polynucleotide encoding the following protein (a) or (b):
   (a) a cytochrome P450 having the amino acid sequence shown by SEQ ID: No. 1 or
   (b) a cytochrome P450 having the amino acid sequence shown by SEQ ID No. 4.

2. An isolated polynucleotide encoding cytochrome P450 having the nucleotide sequence shown by SEQ ID No. 2.

3. An isolated polynucleotide encoding cytochrome P450 having the nucleotide sequence shown by SEQ ID No. 3.

4. An isolated polynucleotide encoding cytochrome P450 having the nucleotide sequence shown by SEQ ID No. 5.

5. An isolated polynucleotide encoding cytochrome P450 having the nucleotide sequence shown by SEQ ID No. 6.

6. A vector comprising the cytochrome P450 of any one of claims 1 to 5.

7. A transformant comprising the cytochrome P450 isolated polynucleotide of any one of claims 1 to 5 in a host cell.

8. A transformant comprising the vector of claim 6 in a host cell.

9. A method for producing a cytochrome P450 comprising the steps of:

incubating the transformant of claim 7; and allowing said transformant to produce a cytochrome P450.

10. A method for producing a cytochrome P450 comprising the steps of incubating the transformant of claim 8 and allowing said transformant to produce the cytochrome P450.

* * * * *

SEQUENCE LISTING

<160> NUMBER OF SEQ ID NOS: 6

<210> SEQ ID NO 1
<211> LENGTH: 524
<212> TYPE: PRT
<213> ORGANISM: Coprinus cinereus
<220> FEATURE:
<221> NAME/KEY: VARIANT
<222> LOCATION: (26)
<223> OTHER INFORMATION: Xaa=Leu or Phe

<400> SEQUENCE: 1

Met Thr Thr Thr Ser Ser Ser Ile Phe Ala Gly Leu Gly Cys Leu Leu
 1               5                  10                  15

Val Ala Ser Ile Ile Tyr Phe Arg Lys Xaa Lys Ala Asn Pro Ala Arg
            20                  25                  30

Ala His Leu Pro Pro Gly Pro Lys Pro Ile Pro Val Leu Gly Asn Val
        35                  40                  45

Lys Asp Leu Arg Ala Lys Glu Leu Trp Leu Pro Ala Met Asp Trp Ala
    50                  55                  60

Lys Gln Tyr Gly Asp Ile Thr Tyr Leu His Val Phe Gly Gln Gly Leu
65                  70                  75                  80

Thr Phe Ile Asn Ser Leu Glu Ser Ala Ser Asp Leu Leu Glu Lys Arg
                85                  90                  95

Gly Gly Met Tyr Ala Asp Lys Pro Gln Phe Thr Met Val Cys Glu Leu
            100                 105                 110

Cys Asn Cys Lys Asn Met Val Ala Phe Thr Pro Tyr Gly Glu Gln Ser
        115                 120                 125

Lys Arg Gln Arg Arg Leu Met His Lys Ala Phe Ala Pro Ala Arg Ile
    130                 135                 140

Pro Asp Tyr His Pro Leu Met Glu Ser Ser Thr Asn Leu Phe Leu Arg
145                 150                 155                 160

Asn Val Ile Ala Ser Pro Ala Asp Tyr Ile Gly His Val Arg Arg Tyr
            165                 170                 175

Ser Gly Ser Leu Thr Leu Asn Ile Val Tyr Gly Tyr Glu Val Thr Ser
            180                 185                 190

Asn Glu Asp Glu Tyr Leu Met Met Ala Glu Cys Val Gly Ile Leu
    195                 200                 205

Ala Asn Glu Ile Ala Ser Ala Gly Gly Val Trp Ala Val Asp Val Met
    210                 215                 220

Pro Phe Leu Ala Lys Ile Pro Lys Trp Ala Glu Gly Leu Pro Gly Met
225                 230                 235                 240

Ser Phe Lys Arg Lys Ala Arg Lys Trp Lys Met Met Glu Asp Trp
            245                 250                 255

Val Asp Gly Pro Phe Glu Tyr Val Lys Asn Thr Met Lys Ser Gly Thr
            260                 265                 270

Tyr Lys Gln Ser Phe Cys Ser Ser Leu Leu Asp Asp Glu Ser Ile Ser
            275                 280                 285

Gln Thr Gln Glu His Phe Glu Phe Asp Leu Lys Trp Thr Ala Asn Ser
            290                 295                 300

Met Tyr Ala Ala Ser Ile Asp Thr Thr Ile Thr Ser Val Ala His Phe
305                 310                 315                 320

Leu Leu Ala Met Met Lys His Pro Glu Val Leu Lys Lys Ala Gln His
                325                 330                 335

Glu Ile Asp Thr Val Val Gly Gln Asp Arg Leu Pro Thr Phe Ser Asp
            340                 345                 350

Arg Lys Ser Leu Pro Tyr Val Glu Ala Val Leu Ser Glu Thr Trp Arg
            355                 360                 365

Trp Ala Ser Pro Val Pro Leu Ser Leu Pro His Lys Leu Thr Glu Asp
370                 375                 380

Asp Val Tyr Arg Gly Met Tyr Ile Pro Lys Gly Ser Leu Ile Phe Ala
385                 390                 395                 400

Asn Ile Trp Ala Met Thr Arg Asp Glu Arg Ile Phe Pro Asp Pro Glu
                405                 410                 415

Thr Phe Asn Pro Glu Arg Tyr Leu Asn Met Asp Pro Glu Thr Lys Lys
            420                 425                 430

Lys Gln Asp Pro Arg Asn Phe Ile Phe Gly Phe Gly Arg Arg Leu Cys
            435                 440                 445

Pro Gly Asn His Ile Val Asp Ala Ser Leu Trp Leu Leu Val Val Arg
    450                 455                 460

Met Met Ala Thr Leu Asp Ile Ser Thr Pro Val Asp Glu Lys Gly Asn
465                 470                 475                 480

Ala Ile Asp Ile Val Pro Val Phe Asp Asn Pro Ile Phe Arg Thr Pro
                485                 490                 495

Asn Pro Phe Pro Cys Asp Met Arg Pro Arg Ser Glu Lys Ala Val Asn
            500                 505                 510

Leu Ile Arg Gln Tyr Ala Asp Pro Arg Ala Ser Ala
    515                 520                 524

<210> SEQ ID NO 2
<211> LENGTH: 4364
<212> TYPE: DNA
<213> ORGANISM: Coprinus cinereus
<220> FEATURE:
<221> NAME/KEY: intron

```
<222> LOCATION: (1229)..(1285)
<220> FEATURE:
<221> NAME/KEY: intron
<222> LOCATION: (1575)..(1874)
<220> FEATURE:
<221> NAME/KEY: intron
<222> LOCATION: (2008)..(2063)
<220> FEATURE:
<221> NAME/KEY: intron
<222> LOCATION: (2083)..(2139)
<220> FEATURE:
<221> NAME/KEY: intron
<222> LOCATION: (2590)..(2639)
<220> FEATURE:
<221> NAME/KEY: intron
<222> LOCATION: (2772)..(2827)
<220> FEATURE:
<221> NAME/KEY: intron
<222> LOCATION: (2967)..(3015)
<220> FEATURE:
<221> NAME/KEY: intron
<222> LOCATION: (3067)..(3120)
<220> FEATURE:
<221> NAME/KEY: intron
<222> LOCATION: (3203)..(3254)
<220> FEATURE:
<221> NAME/KEY: intron
<222> LOCATION: (3384)..(3441)
<220> FEATURE:
<221> NAME/KEY: intron
<222> LOCATION: (3586)..(3641)

<400> SEQUENCE: 2
atggccccga aagaaattc tcgcgtgtca gtcgcccctg catacagaaa gacaaatgaa      60
tggattgagg tcgatgcggc gaggaatgaa cagacctagc ataggacga tcgtggcaga    120 ttggagagga aggttattcg ttgaacgtta cccgcctgct tcccttgaa atcggtttcc    180 gtagtgtcgg gatcggaacg agaggagaaa catcatgcga agacgaaag aaggtcgaca    240 ttccatcaca gcaatctgat accctcttgg ggagcaggcg acagaatctc gtcactgata    300
gagctcgaag ctacattgag atcggtgtta acgtcgatcc agagattgga cagtcggagt    360
ctggcaagag agggcggtcc aagttcgaag aatttcgtat cggcgggcga caataggga    420 attatggaca gtgagcaggc caggttcgag ccatggtctg gagtgattca gcccagataa    480
ccaagaagtc gagtatgggt ggttgtgggg gtagaaaggt gggagaacat gaggactgtg    540
cagtcaggac ctgatgataa tgcgatagaa gccagttaag cattcggaca agggcgaact    600
ccagaacgtg cggtggttgt gctgcgtttc caggcggtgt gcagggtaaa ccgtgacacg    660
tcagagagag actgtgtgat taaagacatg gtcccatcag cttcgctgtc tcgacacaat    720
attgtgcttc tttttgcgcg cgactgtga tctgtttcgt gaaaacagat tcctgcaaaa    780
gacttttcat cttggcaagt ggaggatgac aggccagaaa gagcaacagc aacggaaagg    840
ttggccgctc gatcttcgat ttggttccgt tgggccggt gcaacggggc agcgccgtaa    900
gagaaattaa attagggtgg tgtttgtcca taacgggatt ccgtccgaat ggggagaagg    960
ggtgttttct gtttccagat tgtgggtgcc gatggataaa tggccaaat ctggcgagat    1020 gggtgtttat gagactgggg ttgtcactga cataacttcg gcttctcgtc ttctcagcca   1080
aaaaaattag cctttttctc aatacgcgtc aatccaaatc ctttaagacc cagttaccgc   1140
ccctctcccc tattcgtttt cccctcctc ccatttccca cccgtcgtcg ctctcttccc    1200
tttcctcgct gccgagtcca tcttcaaggt acctatatca tatcttcctc gcctaatagg   1260
agtcttctca tcgtcgtcga cgtagcgtat cacctcccgt tccgtcatc aacggctcag    1320 agaagagaac ttggtctata gcgttcattg ttccttcatc ttccctcaaa ct atg aca   1378
```

```
                                                Met Thr
                                                  1
acg acg agc agt agt atc ttc gct ggt cta gga tgc ctt ctt gtc gcc    1426
Thr Thr Ser Ser Ser Ile Phe Ala Gly Leu Gly Cys Leu Leu Val Ala
          5                  10                  15 tcc atc att tac ttc cgg aag ttt aaa gct aac ccg gca cga gct cac    1474
Ser Ile Ile Tyr Phe Arg Lys Phe Lys Ala Asn Pro Ala Arg Ala His
     20                  25                  30 ctc cct cct ggt ccc aaa ccc att ccc gta ctc ggc aac gtc aaa gac    1522
Leu Pro Pro Gly Pro Lys Pro Ile Pro Val Leu Gly Asn Val Lys Asp
 35                  40                  45                  50 ctt cga gcg aaa gag cta tgg ctg ccg gcg atg gac tgg gcg aag caa    1570
Leu Arg Ala Lys Glu Leu Trp Leu Pro Ala Met Asp Trp Ala Lys Gln
              55                  60                  65 tac g gtgagcctct tcaacttgtg ccttgggcga tatttcgttt ggaatggcgg       1624
Tyr tgtaggagtt cgccgccatg acgtcccgc aaagggtgga attaatgctc gcctttgcaa   1684
atggcgagta gcttcaacgt gccataatgt acctcatacg agttatatag cctcagtaat  1744
gctgagctaa ctcctcggtc gactccactg acgctttggc ttccgggcac gaggctaggg  1804
gtggatacca acgtattctc gaagacgttc tcgtttgag ccctatacta acgcgctggg   1864
cttatactag gc gat atc acc tac ctt cac gtc ttt gga caa ggt ctc      1912
            Gly Asp Ile Thr Tyr Leu His Val Phe Gly Gln Gly Leu
                 70                  75                  80 aca ttt atc aac tcc ttg gaa tct gca agc gac ttg ctc gag aaa cga    1960
Thr Phe Ile Asn Ser Leu Glu Ser Ala Ser Asp Leu Leu Glu Lys Arg
                 85                  90                  95 ggc ggc atg tac gcc gac aaa cct cag ttt acc atg gtt tgc gaa ct g   2008
Gly Gly Met Tyr Ala Asp Lys Pro Gln Phe Thr Met Val Cys Glu Leu
             100                 105                 110 taagtctttt tgtcgcttct ccactaccag gtgactgaac gcgaccggcc cttag g tgc 2067
                                                              Cys aac tgt aag aat atg gtcagtcctt ctctaaccga caaagcgagc gatcctgagc    2122
Asn Cys Lys Asn Met
        115 tctatccact tttgcag gtt gcc ttt acg ccc tac gga gaa cag tcg aag     2172
                Val Ala Phe Thr Pro Tyr Gly Glu Gln Ser Lys
                             120                 125 cga caa cgg cga ttg atg cac aaa gct ttc gcc cct gct cgc atc ccg    2220
Arg Gln Arg Arg Leu Met His Lys Ala Phe Ala Pro Ala Arg Ile Pro
130                 135                 140                 145 gat tat cat ccc tta atg gaa tca tca acc aac ctc ttc ctc cga aac    2268
Asp Tyr His Pro Leu Met Glu Ser Ser Thr Asn Leu Phe Leu Arg Asn
                 150                 155                 160 gtc att gca tcc ccg gcc gat tat atc ggt cac gta cga agg tac tct    2316
Val Ile Ala Ser Pro Ala Asp Tyr Ile Gly His Val Arg Arg Tyr Ser
                 165                 170                 175 ggt tca ctc acg ctc aac att gtc tat ggg tac gaa gtc act tcc aac    2364
Gly Ser Leu Thr Leu Asn Ile Val Tyr Gly Tyr Glu Val Thr Ser Asn
             180                 185                 190 gaa gac gaa tat ctt atg atg gcg gag gag tgt gtc ggt att ctc gct    2412
Glu Asp Glu Tyr Leu Met Met Ala Glu Glu Cys Val Gly Ile Leu Ala
195                 200                 205 aac gaa att gcg agt gct gga ggt gtt tgg gct gtc gat gtc atg cct    2460
Asn Glu Ile Ala Ser Ala Gly Gly Val Trp Ala Val Asp Val Met Pro
210                 215                 220                 225 ttc ctc gct aag atc cct aaa tgg gca gag gga ttg cca gga atg agc    2508
Phe Leu Ala Lys Ile Pro Lys Trp Ala Glu Gly Leu Pro Gly Met Ser
```

```
                  230                 235                 240
ttt aaa cgg aag gcg agg aag tgg aag aag atg atg gag gat tgg gtt      2556
Phe Lys Arg Lys Ala Arg Lys Trp Lys Lys Met Met Glu Asp Trp Val
            245                 250                 255 gat gga cca ttc gaa tac gtc aag aac acc atg gtaagcttct ttcatatcaa    2609
Asp Gly Pro Phe Glu Tyr Val Lys Asn Thr Met
        260                 265 ctcatcaacg tttaattaat tctccaacag aaa agc ggc act tac aag caa tca     2663
                                 Lys Ser Gly Thr Tyr Lys Gln Ser
                                                 270             275 ttc tgc tct tcc cta tta gac gat gaa agt atc tcg caa acc cag gag      2711
Phe Cys Ser Ser Leu Leu Asp Asp Glu Ser Ile Ser Gln Thr Gln Glu
            280                 285                 290 cac ttc gaa ttt gac ttg aag tgg acg gct aac tcg atg tat gca gcc      2759
His Phe Glu Phe Asp Leu Lys Trp Thr Ala Asn Ser Met Tyr Ala Ala
            295                 300                 305 agc atc gat act gtgcgtgatc atacccgata tcaagttaat tgtcgcctga          2811
Ser Ile Asp Thr
    310 cccccgccatc ttttag acg att acc tca gtc gct cac ttc cta ctt gca atg   2863
                   Thr Ile Thr Ser Val Ala His Phe Leu Leu Ala Met
                                    315                 320 atg aag cac ccc gaa gtc ttg aag aag gcg cag cat gaa atc gat acc      2911
Met Lys His Pro Glu Val Leu Lys Lys Ala Gln His Glu Ile Asp Thr
325                 330                 335                 340 gtt gtc gga caa gat cgc ctc cct acc ttc agc gac agg aag tct ttg      2959
Val Val Gly Gln Asp Arg Leu Pro Thr Phe Ser Asp Arg Lys Ser Leu
            345                 350                 355 cca tat g gtacgttcca tgatagtccg actgaatgtc cacttatttg gtcgtgcag tt   3017
Pro Tyr                                                         Val gaa gcc gtc ctc tcc gag act tgg aga tgg gct tcc ccc gtc cca ttg      3065
Glu Ala Val Leu Ser Glu Thr Trp Arg Trp Ala Ser Pro Val Pro Leu
360                 365                 370                 375 a gtgagtagga tagtacctct ttgcacacgg ccaaactcag tcccacgac cttag gc     3122
                                                               Ser ttg cct cat aaa ttg act gaa gat gac gtg tat cga gga atg tat atc      3170
Leu Pro His Lys Leu Thr Glu Asp Asp Val Tyr Arg Gly Met Tyr Ile
            380                 385                 390 ccg aag ggt tcc ttg atc ttc gcc aat atc tg gtaagctcca ttgaactcca     3222
Pro Lys Gly Ser Leu Ile Phe Ala Asn Ile Trp
            395                 400 ggtttagcgg gccattctaa tcctctttga ag g gcg atg aca cga gat gag cgc    3276
                                     Ala Met Thr Arg Asp Glu Arg
                                                 405             410 atc ttc ccc gac ccg gag acg ttc aat ccc gag aga tac ttg aac atg      3324
Ile Phe Pro Asp Pro Glu Thr Phe Asn Pro Glu Arg Tyr Leu Asn Met
            415                 420                 425 gat cca gag acc aag aag aag caa gat cca cgg aac ttc atc ttc gga      3372
Asp Pro Glu Thr Lys Lys Lys Gln Asp Pro Arg Asn Phe Ile Phe Gly
            430                 435                 440 ttc ggt cga ag gtttgtccac gcatgctggc tgcaactgga atctgcaact           3423
Phe Gly Arg Arg
        445 gactgtcatt cgccttag g ctt tgc cct gga aat cat atc gta gat gct tcg    3475
                     Leu Cys Pro Gly Asn His Ile Val Asp Ala Ser
                                         450                 455 ctg tgg ctg ttg gtc gtt cgc atg atg gct acc ctt gat atc tct acc      3523
Leu Trp Leu Leu Val Val Arg Met Met Ala Thr Leu Asp Ile Ser Thr
460                 465                 470
```

-continued

```
ccc gtc gac gag aaa ggc aat gca att gat att gtt ccg gtt ttc gac      3571
Pro Val Asp Glu Lys Gly Asn Ala Ile Asp Ile Val Pro Val Phe Asp
        475                 480                 485 aac cct atc ttc ag gttcgccgc atccgtcccc tggttactct gtactgaatg        3625
Asn Pro Ile Phe Arg
490 tcttttctca tgctag a acg cca aat ccc ttc ccc tgc gat atg cga cca cgt  3678
               Thr Pro Asn Pro Phe Pro Cys Asp Met Arg Pro Arg
                   495                 500                 505 tcc gag aag gct gta aat ctc att cga caa tac gcc gac cct cgc gcc      3726
Ser Glu Lys Ala Val Asn Leu Ile Arg Gln Tyr Ala Asp Pro Arg Ala
                510                 515                 520 tct gca taatcttctg tcagccatat acaaactacg acctcgctca cagccgcgga       3782
Ser Ala ctcttcgaca ctggccttttt cgagcttata tgaccggaat tatcactcta gggatctgtc   3842
caaaaggtta agcgacgatt gaattttttca gacatttttg catctcttcc cacttctagc   3902
cttagattta aagttctacg gggcacagta tcacctccat ctttttttctc aattatcctt   3962 gttcggtccc ggatggcaca ttctttatat cagccatggt cactcctttc tctatctcgc    4022
tccctacatt tccacccatt tatcattatg acctgcattc atctcgaata cccacaggat    4082
aggacggttc ggcgctttga ttaaattacg actcgcatct agcgtatact gtacaccttc    4142
attaccgtag tcgtcacctt tcaaccagaa acgcctcgaa acaccgcaca ccgcgtgtac    4202
tttcagtgtt aagtggaaat tcagatcttt ccaacctcgg gctttggatg tgatatttga    4262
atctcggaga cgatgaagcg agcggagact cctttgcgag gttttttggtg ctcgatgctt   4322 ctattcccgt tgctgccttt atcagttcca acttctgcgt ca                      4364

<210> SEQ ID NO 3
<211> LENGTH: 2236
<212> TYPE: DNA
<213> ORGANISM: Coprinus cinereus
<220> FEATURE:
<221> NAME/KEY: CDS
<222> LOCATION: (162)..(1736)

<400> SEQUENCE: 3
cgttttcccc ctcctcccat ttcccacccg tcgtcgctct cttcccttttc ctcgctgccg    60 agtccatctt caagcgtatc acctcccgtt cccgtcatca acggcgcaga gaagagaact   120
tggtctatag cgttcattgt tccttcatct tccctcaaac t atg aca acg acg agc   176
                                              Met Thr Thr Thr Ser
                                                  1               5 agt agt atc ttc gct ggt cta gga tgc ctt ctt gtc gcc tcc atc att      224
Ser Ser Ile Phe Ala Gly Leu Gly Cys Leu Leu Val Ala Ser Ile Ile
            10                  15                  20 tac ttc cgg aag ctt aaa gct aac ccg gca cga gct cac ctc cct cct      272
Tyr Phe Arg Lys Leu Lys Ala Asn Pro Ala Arg Ala His Leu Pro Pro
        25                  30                  35 ggt ccc aaa ccc att ccc gta ctc ggc aac gtc aaa gac ctt cga gcg      320
Gly Pro Lys Pro Ile Pro Val Leu Gly Asn Val Lys Asp Leu Arg Ala
    40                  45                  50 aaa gag cta tgg ctg ccg gcg atg gac tgg gcg aag caa tac ggc gat      368
Lys Glu Leu Trp Leu Pro Ala Met Asp Trp Ala Lys Gln Tyr Gly Asp
55                  60                  65 atc acc tac ctt cac gtc ttt gga caa ggt ctc aca ttt atc aac tcc      416
Ile Thr Tyr Leu His Val Phe Gly Gln Gly Leu Thr Phe Ile Asn Ser
70                  75                  80                  85
```

-continued

| | |
|---|---|
| ttg gaa tct gca agc gac ttg ctc gag aaa cga ggc ggc atg tac gcc<br>Leu Glu Ser Ala Ser Asp Leu Leu Glu Lys Arg Gly Gly Met Tyr Ala<br>               90                      95                   100 | 464 |
| gac aaa cct cag ttt acc atg gtt tgc gaa ctg tgc aac tgt aag aat<br>Asp Lys Pro Gln Phe Thr Met Val Cys Glu Leu Cys Asn Cys Lys Asn<br>         105                   110                  115 | 512 |
| atg gtt gcc ttt acg ccc tac gga gaa cag tcg aag cga caa cgg cga<br>Met Val Ala Phe Thr Pro Tyr Gly Glu Gln Ser Lys Arg Gln Arg Arg<br>         120                   125                  130 | 560 |
| ttg atg cac aaa gct ttc gcc cct gct cgc atc ccg gat tat cat ccc<br>Leu Met His Lys Ala Phe Ala Pro Ala Arg Ile Pro Asp Tyr His Pro<br>          135                  140                 145 | 608 |
| tta atg gaa tca tca acc aac ctc ttc ctc cga aac gtc att gca tcc<br>Leu Met Glu Ser Ser Thr Asn Leu Phe Leu Arg Asn Val Ile Ala Ser<br>150                  155                 160               165 | 656 |
| ccg gcc gat tat atc ggt cac gta cga agg tac tct ggt tca ctc acg<br>Pro Ala Asp Tyr Ile Gly His Val Arg Arg Tyr Ser Gly Ser Leu Thr<br>                170                 175               180 | 704 |
| ctc aac att gtc tat ggg tac gaa gtc act tcc aac gaa gac gaa tat<br>Leu Asn Ile Val Tyr Gly Tyr Glu Val Thr Ser Asn Glu Asp Glu Tyr<br>                  185                 190              195 | 752 |
| ctt atg atg gcg gag gag tgt gtc ggt att ctc gct aac gaa att gcg<br>Leu Met Met Ala Glu Glu Cys Val Gly Ile Leu Ala Asn Glu Ile Ala<br>         200                   205                  210 | 800 |
| agt gct gga ggt gtt tgg gct gtc gat gtc atg cct ttc ctc gct aag<br>Ser Ala Gly Gly Val Trp Ala Val Asp Val Met Pro Phe Leu Ala Lys<br>          215                  220                 225 | 848 |
| atc cct aaa tgg gca gag gga ttg cca gga atg agc ttt aaa cgg aag<br>Ile Pro Lys Trp Ala Glu Gly Leu Pro Gly Met Ser Phe Lys Arg Lys<br>230                  235                 240               245 | 896 |
| gcg agg aag tgg aag aag atg atg gag gat tgg gtt gat gga cca ttc<br>Ala Arg Lys Trp Lys Lys Met Met Glu Asp Trp Val Asp Gly Pro Phe<br>                  250                 255               260 | 944 |
| gaa tac gtc aag aac acc atg aaa agc ggc act tac aag caa tca ttc<br>Glu Tyr Val Lys Asn Thr Met Lys Ser Gly Thr Tyr Lys Gln Ser Phe<br>                265                 270               275 | 992 |
| tgc tct tcc cta tta gac gat gaa agt atc tcg caa acc cag gag cac<br>Cys Ser Ser Leu Leu Asp Asp Glu Ser Ile Ser Gln Thr Gln Glu His<br>         280                   285                  290 | 1040 |
| ttc gaa ttt gac ttg aag tgg acg gct aac tcg atg tat gca gcc agc<br>Phe Glu Phe Asp Leu Lys Trp Thr Ala Asn Ser Met Tyr Ala Ala Ser<br>          295                  300                 305 | 1088 |
| atc gat act acg att acc tca gtc gct cac ttc cta ctt gca atg atg<br>Ile Asp Thr Thr Ile Thr Ser Val Ala His Phe Leu Leu Ala Met Met<br>310                  315                 320               325 | 1136 |
| aag cac ccc gaa gtc ttg aag aag gca cag cat gaa atc gat acc gtt<br>Lys His Pro Glu Val Leu Lys Lys Ala Gln His Glu Ile Asp Thr Val<br>                330                 335               340 | 1184 |
| gtc gga caa gat cgc ctc ccc acc ttc agc gac agg aag tct ttg cca<br>Val Gly Gln Asp Arg Leu Pro Thr Phe Ser Asp Arg Lys Ser Leu Pro<br>         345                  350                355 | 1232 |
| tat gtt gaa gcc gtc ctc tcc gag act tgg aga tgg gct tcc ccc gtc<br>Tyr Val Glu Ala Val Leu Ser Glu Thr Trp Arg Trp Ala Ser Pro Val<br>          360                  365                370 | 1280 |
| cca ttg agc ttg cct cat aaa ttg act gaa gat gac gtg tat cga gga<br>Pro Leu Ser Leu Pro His Lys Leu Thr Glu Asp Asp Val Tyr Arg Gly<br>375                  380                 385 | 1328 |
| atg tat atc ccg aag ggt tcc ttg atc ttc gcc aat atc tgg gcg atg<br>Met Tyr Ile Pro Lys Gly Ser Leu Ile Phe Ala Asn Ile Trp Ala Met<br>390                  395                 400               405 | 1376 |

-continued

```
aca cga gat gag cgc atc ttc ccc gac ccg gag acg ttc aat ccc gag    1424
Thr Arg Asp Glu Arg Ile Phe Pro Asp Pro Glu Thr Phe Asn Pro Glu
                410                 415                 420 aga tac ttg aac atg gat cca gag acc aag aag aag caa gat cca cgg    1472
Arg Tyr Leu Asn Met Asp Pro Glu Thr Lys Lys Lys Gln Asp Pro Arg
            425                 430                 435 aac ttc atc ttc gga ttc ggt cga agg ctt tgc cct gga aat cat atc    1520
Asn Phe Ile Phe Gly Phe Gly Arg Arg Leu Cys Pro Gly Asn His Ile
        440                 445                 450 gta gat gct tcg ctg tgg ctg ttg gtc gtt cgc atg atg gct acc ctt    1568
Val Asp Ala Ser Leu Trp Leu Leu Val Val Arg Met Met Ala Thr Leu
    455                 460                 465 gat atc tct acc ccc gtc gac gag aaa ggc aat gca att gat att gtt    1616
Asp Ile Ser Thr Pro Val Asp Glu Lys Gly Asn Ala Ile Asp Ile Val
470                 475                 480                 485 ccg gtt ttc gac aac cct atc ttc aga acg cca aat ccc ttc ccc tgc    1664
Pro Val Phe Asp Asn Pro Ile Phe Arg Thr Pro Asn Pro Phe Pro Cys
                490                 495                 500 gat atg cga cca cgt tcc gag aag gct gta aat ctc att cga caa tac    1712
Asp Met Arg Pro Arg Ser Glu Lys Ala Val Asn Leu Ile Arg Gln Tyr
            505                 510                 515 gcc gac cct cgc gcc tct gca taatcttctg tcagccatat acaaactacg       1763
Ala Asp Pro Arg Ala Ser Ala
        520 acctcgctca cagccgcgga ctcttcgaca ctggcctttt cgagcttata tgaccggaat  1823 tatcactcta gggatctgtc caaaaggtta agcgacgatt gaattttttca gacatttttg 1883 catctcttcc cacttctagc cttagattta aagttctacg gggcacagta tcacctccat  1943 cttttttctc aattatcctt gttcggtccc ggatggcaca ttctttatat cagccatggt  2003 cactcctttc tctatctcgc tccctacatt tccacccatt tatcattatg acctgcattc  2063 atctcgaata cccacaggat aggacggttc ggcgctttga ttaaattacg actcgcatct  2123 agcgtatact gtacaccttc attaccgtag tcgtcacctt tcaaccagaa acgcctcgaa  2183 acaaaaaaaa aaaaaaaaa aaaaaaagt actctgcgtt gataccactg ctt           2236
```

<210> SEQ ID NO 4
<211> LENGTH: 506
<212> TYPE: PRT
<213> ORGANISM: Coprinus cinereus
<220> FEATURE:
<221> NAME/KEY: VARIANT
<222> LOCATION: (26)
<223> OTHER INFORMATION: Xaa=Leu or Phe

<400> SEQUENCE: 4

```
Met Thr Thr Thr Ser Ser Ser Ile Phe Ala Gly Leu Gly Cys Leu Leu
  1               5                  10                  15

Val Ala Ser Ile Ile Tyr Phe Arg Lys Xaa Lys Ala Asn Pro Ala Arg
                 20                  25                  30

Ala His Leu Pro Pro Gly Pro Lys Pro Ile Pro Val Leu Gly Asn Val
             35                  40                  45

Lys Asp Leu Arg Ala Lys Glu Leu Trp Leu Pro Ala Met Asp Trp Ala
         50                  55                  60

Lys Gln Tyr Gly Asp Ile Thr Tyr Leu His Val Phe Gly Gln Gly Leu
 65                  70                  75                  80

Thr Phe Ile Asn Ser Leu Glu Ser Ala Ser Asp Leu Leu Glu Lys Arg
                 85                  90                  95
```

-continued

```
Gly Gly Met Tyr Ala Asp Lys Pro Gln Phe Thr Met Val Cys Glu Leu
            100                 105                 110
Cys Asn Cys Lys Asn Met Val Ala Phe Thr Pro Tyr Gly Glu Gln Ser
            115                 120                 125
Lys Arg Gln Arg Arg Leu Met His Lys Ala Phe Ala Pro Ala Arg Ile
        130                 135                 140
Pro Asp Tyr His Pro Leu Met Glu Ser Ser Thr Asn Leu Phe Leu Arg
145                 150                 155                 160
Asn Val Ile Ala Ser Pro Ala Asp Tyr Ile Gly His Val Arg Arg Tyr
                165                 170                 175
Ser Gly Ser Leu Thr Leu Asn Ile Val Tyr Gly Tyr Glu Val Thr Ser
            180                 185                 190
Asn Glu Asp Glu Tyr Leu Met Met Ala Glu Glu Cys Val Gly Ile Leu
        195                 200                 205
Ala Asn Glu Ile Ala Ser Ala Gly Gly Val Trp Ala Val Asp Val Met
        210                 215                 220
Pro Phe Leu Ala Lys Ile Pro Lys Trp Ala Glu Gly Leu Pro Gly Met
225                 230                 235                 240
Ser Phe Lys Arg Lys Ala Arg Lys Trp Lys Met Met Glu Asp Trp
                245                 250                 255
Val Asp Gly Pro Phe Glu Tyr Val Lys Asn Thr Met Lys Ser Gly Thr
            260                 265                 270
Tyr Lys Gln Ser Phe Cys Ser Ser Leu Leu Asp Asp Glu Ser Ile Ser
        275                 280                 285
Gln Thr Gln Glu His Phe Glu Phe Asp Leu Lys Trp Thr Ala Asn Ser
        290                 295                 300
Met Tyr Ala Ala Ser Ile Asp Thr Thr Ile Thr Ser Val Ala His Phe
305                 310                 315                 320
Leu Leu Ala Met Met Lys His Pro Glu Val Leu Lys Lys Ala Gln His
                325                 330                 335
Glu Ile Asp Thr Val Val Gly Gln Asp Arg Leu Pro Thr Phe Ser Asp
            340                 345                 350
Arg Lys Ser Leu Pro Tyr Val Glu Ala Val Leu Ser Glu Thr Trp Arg
        355                 360                 365
Trp Ala Ser Pro Val Pro Leu Ser Leu Pro His Lys Leu Thr Glu Asp
        370                 375                 380
Asp Val Tyr Arg Gly Met Tyr Ile Pro Lys Gly Ser Leu Ile Phe Ala
385                 390                 395                 400
Asn Ile Trp Ala Met Thr Arg Asp Glu Arg Ile Phe Pro Asp Pro Glu
                405                 410                 415
Thr Phe Asn Pro Glu Arg Tyr Leu Asn Met Asp Pro Glu Thr Lys Lys
            420                 425                 430
Lys Gln Asp Pro Arg Asn Phe Ile Phe Gly Phe Arg Arg Leu Cys
        435                 440                 445
Pro Gly Asn His Ile Val Asp Ala Ser Leu Trp Leu Leu Val Val Arg
        450                 455                 460
Met Met Ala Thr Leu Asp Ile Ser Thr Pro Val Asp Glu Lys Gly Asn
465                 470                 475                 480
Ala Ile Asp Ile Val Pro Val Phe Asp Asn Pro Ile Phe Arg Thr Pro
                485                 490                 495
Asn Pro Phe Pro Cys Asp Met Arg Pro Arg
            500                 505 506
```

-continued

```
<210> SEQ ID NO 5
<211> LENGTH: 4360
<212> TYPE: DNA
<213> ORGANISM: Coprinus cinereus
<220> FEATURE:
<221> NAME/KEY: intron
<222> LOCATION: (1229)..(1285)
<220> FEATURE:
<221> NAME/KEY: intron
<222> LOCATION: (1575)..(1874)
<220> FEATURE:
<221> NAME/KEY: intron
<222> LOCATION: (2008)..(2063)
<220> FEATURE:
<221> NAME/KEY: intron
<222> LOCATION: (2083)..(2139)
<220> FEATURE:
<221> NAME/KEY: intron
<222> LOCATION: (2590)..(2639)
<220> FEATURE:
<221> NAME/KEY: intron
<222> LOCATION: (2772)..(2827)
<220> FEATURE:
<221> NAME/KEY: intron
<222> LOCATION: (2967)..(3015)
<220> FEATURE:
<221> NAME/KEY: intron
<222> LOCATION: (3067)..(3120)
<220> FEATURE:
<221> NAME/KEY: intron
<222> LOCATION: (3203)..(3254)
<220> FEATURE:
<221> NAME/KEY: intron
<222> LOCATION: (3384)..(3441)
<220> FEATURE:
<221> NAME/KEY: intron
<222> LOCATION: (3586)..(3641)

<400> SEQUENCE: 5
atggccccga aagaaattc  tcgcgtgtca gtcgcccctg catacagaaa gacaaatgaa      60
tggattgagg tcgatgcggc gaggaatgaa cagacctagc ataggacga  tcgtggcaga     120 ttggagagga aggttattcg ttgaacgtta cccgcctgct tcccttttgaa atcggtttcc    180 gtagtgtcgg gatcggaacg agaggagaaa catcatgcga aagacgaaag aaggtcgaca    240
ttccatcaca gcaatctgat accctcttgg ggagcaggcg acagaatctc gtcactgata    300
gagctcgaag ctacattgag atcggtgtta acgtcgatcc agagattgga cagtcggagt    360
ctggcaagag agggcggtcc aagttcgaag aatttcgtat cggcgggcga caatagggga    420
attatggaca gtgagcaggc caggttcgag ccatggtctg gagtgattca gcccagataa    480
ccaagaagtc gagtatgggt ggttgtgggg gtagaaaggt gggagaacat gaggactgtg    540
cagtcaggac ctgatgataa tgcgatagaa gccagttaag cattcggaca agggcgaact    600
ccagaacgtg cggtggttgt gctgcgtttc caggcggtgt gcagggtaaa ccgtgacacg    660
tcagagagag actgtgtgat taaagacatg gtcccatcag cttcgctgtc tcgacacaat    720
attgtgcttc tttttgcgcg gcgactgtga tctgtttcgt gaaaacagat tcctgcaaaa    780
gacttttcat cttggcaagt ggaggatgac aggccagaaa gagcaacagc aacgaaaagg    840
ttggccgctc gatcttcgat ttggttccgt tggggccggt gcaacggggc agcgccgtaa    900
gagaaattaa attagggtgg tgtttgtcca taacgggatt ccgtccgaat ggggagaagg    960
ggtgttttct gtttccagat tgtgggtgcc gatggataaa tgggccaaat ctggcgagat   1020
gggtgtttat gagactgggg ttgtcactga cataacttcg gcttctcgtc ttctcagcca   1080
aaaaaattag cctttttctc aatacgcgtc aatccaaatc ctttaagacc cagttaccgc   1140
ccctctcccc tattcgtttt ccccctcctc ccatttccca cccgtcgtcg ctctcttccc   1200
```

-continued

```
tttcctcgct gccgagtcca tcttcaaggt acctatatca tatcttcctc gcctaatagg    1260
agtcttctca tcgtcgtcga cgtagcgtat cacctcccgt tcccgtcatc aacggctcag    1320
agaagagaac ttggtctata gcgttcattg ttccttcatc ttccctcaaa ct atg aca    1378
                                                          Met Thr
                                                            1 acg acg agc agt agt atc ttc gct ggt cta gga tgc ctt ctt gtc gcc    1426
Thr Thr Ser Ser Ser Ile Phe Ala Gly Leu Gly Cys Leu Leu Val Ala
        5                  10                  15 tcc atc att tac ttc cgg aag ttt aaa gct aac ccg gca cga gct cac    1474
Ser Ile Ile Tyr Phe Arg Lys Phe Lys Ala Asn Pro Ala Arg Ala His
 20                  25                  30 ctc cct cct ggt ccc aaa ccc att ccc gta ctc ggc aac gtc aaa gac    1522
Leu Pro Pro Gly Pro Lys Pro Ile Pro Val Leu Gly Asn Val Lys Asp
 35                  40                  45                  50 ctt cga gcg aaa gag cta tgg ctg ccg gcg atg gac tgg gcg aag caa    1570
Leu Arg Ala Lys Glu Leu Trp Leu Pro Ala Met Asp Trp Ala Lys Gln
         55                  60                  65 tac g gtgagcctct tcaacttgtg ccttgggcga tatttcgttt ggaatggcgg    1624
Tyr tgtaggagtt cgccgccatg gacgtcccgc aaagggtgga attaatgctc gcctttgcaa    1684
atggcgagta gcttcaacgt gccataatgt acctcatacg agtatatag cctcagtaat    1744 gctgagctaa ctcctcggtc gactccactg acgctttggc ttccgggcac gaggctaggg    1804
gtggatacca acgtattctc gaagacgttc ctcgtttgag ccctatacta acgcgctggg    1864 cttatacta g gc gat atc acc tac ctt cac gtc ttt gga caa ggt ctc    1912
             Gly Asp Ile Thr Tyr Leu His Val Phe Gly Gln Gly Leu
                  70                  75                  80 aca ttt atc aac tcc ttg gaa tct gca agc gac ttg ctc gag aaa cga    1960
Thr Phe Ile Asn Ser Leu Glu Ser Ala Ser Asp Leu Leu Glu Lys Arg
             85                  90                  95 ggc ggc atg tac gcc gac aaa cct cag ttt acc atg gtt tgc gaa ct g    2008
Gly Gly Met Tyr Ala Asp Lys Pro Gln Phe Thr Met Val Cys Glu Leu
        100                 105                 110 taagtctttt tgtcgcttct ccactaccag gtgactgaac gcgaccggcc cttag g tgc    2067
                                                              Cys aac tgt aag aat atg gtcagtcctt ctctaaccga caaagcgagc gatcctgagc    2122
Asn Cys Lys Asn Met
 115 tctatccact tttgcag gtt gcc ttt acg ccc tac gga gaa cag tcg aag    2172
                Val Ala Phe Thr Pro Tyr Gly Glu Gln Ser Lys
                    120                 125 cga caa cgg cga ttg atg cac aaa gct ttc gcc cct gct cgc atc ccg    2220
Arg Gln Arg Arg Leu Met His Lys Ala Phe Ala Pro Ala Arg Ile Pro
130                 135                 140                 145 gat tat cat ccc tta atg gaa tca tca acc aac ctc ttc ctc cga aac    2268
Asp Tyr His Pro Leu Met Glu Ser Ser Thr Asn Leu Phe Leu Arg Asn
                150                 155                 160 gtc att gca tcc ccg gcc gat tat atc ggt cac gta cga agg tac tct    2316
Val Ile Ala Ser Pro Ala Asp Tyr Ile Gly His Val Arg Arg Tyr Ser
            165                 170                 175 ggt tca ctc acg ctc aac att gtc tat ggg tac gaa gtc act tcc aac    2364
Gly Ser Leu Thr Leu Asn Ile Val Tyr Gly Tyr Glu Val Thr Ser Asn
        180                 185                 190 gaa gac gaa tat ctt atg atg gcg gag gag tgt gtc ggt att ctc gct    2412
Glu Asp Glu Tyr Leu Met Met Ala Glu Glu Cys Val Gly Ile Leu Ala
    195                 200                 205
```

-continued

```
aac gaa att gcg agt gct gga ggt gtt tgg gct gtc gat gtc atg cct    2460
Asn Glu Ile Ala Ser Ala Gly Gly Val Trp Ala Val Asp Val Met Pro
210             215                 220                 225 ttc ctc gct aag atc cct aaa tgg gca gag gga ttg cca gga atg agc    2508
Phe Leu Ala Lys Ile Pro Lys Trp Ala Glu Gly Leu Pro Gly Met Ser
            230                 235                 240 ttt aaa cgg aag gcg agg aag tgg aag aag atg atg gag gat tgg gtt    2556
Phe Lys Arg Lys Ala Arg Lys Trp Lys Lys Met Met Glu Asp Trp Val
        245                 250                 255 gat gga cca ttc gaa tac gtc aag aac acc atg gtaagcttct ttcatatcaa  2609
Asp Gly Pro Phe Glu Tyr Val Lys Asn Thr Met
    260                 265 ctcatcaacg tttaattaat tctccaacag aaa agc ggc act tac aag caa tca   2663
                                 Lys Ser Gly Thr Tyr Lys Gln Ser
                                             270             275 ttc tgc tct tcc cta tta gac gat gaa agt atc tcg caa acc cag gag    2711
Phe Cys Ser Ser Leu Leu Asp Asp Glu Ser Ile Ser Gln Thr Gln Glu
            280                 285                 290 cac ttc gaa ttt gac ttg aag tgg acg gct aac tcg atg tat gca gcc    2759
His Phe Glu Phe Asp Leu Lys Trp Thr Ala Asn Ser Met Tyr Ala Ala
        295                 300                 305 agc atc gat act gtgcgtgatc atacccgata tcaagttaat tgtcgcctga       2811
Ser Ile Asp Thr
    310 ccccgccatc ttttag acg att acc tca gtc gct cac ttc cta ctt gca atg 2863
               Thr Ile Thr Ser Val Ala His Phe Leu Leu Ala Met
                           315                 320 atg aag cac ccc gaa gtc ttg aag aag gcg cag cat gaa atc gat acc   2911
Met Lys His Pro Glu Val Leu Lys Lys Ala Gln His Glu Ile Asp Thr
325             330                 335                 340 gtt gtc gga caa gat cgc ctc cct acc ttc agc gac agg aag tct ttg   2959
Val Val Gly Gln Asp Arg Leu Pro Thr Phe Ser Asp Arg Lys Ser Leu
            345                 350                 355 cca tat g gtacgttcca tgatagtccg actgaatgtc cacttatttg gtcgtgca g tt 3017
Pro Tyr                                                         Val gaa gcc gtc ctc tcc gag act tgg aga tgg gct tcc ccc gtc cca ttg   3065
Glu Ala Val Leu Ser Glu Thr Trp Arg Trp Ala Ser Pro Val Pro Leu
360             365                 370                 375 a gtgagtagga tagtacctct ttgcacacgg ccaaactcag tcccacgacc ttag gc  3122
                                                              Ser ttg cct cat aaa ttg act gaa gat gac gtg tat cga gga atg tat atc  3170
Leu Pro His Lys Leu Thr Glu Asp Asp Val Tyr Arg Gly Met Tyr Ile
            380                 385                 390 ccg aag ggt tcc ttg atc ttc gcc aat atc tg g taagctccat tgaactccag 3223
Pro Lys Gly Ser Leu Ile Phe Ala Asn Ile Trp
        395                 400 gtttagcggg ccattctaat cctctttgaa g g gcg atg aca cga gat gag cgc  3276
                                    Ala Met Thr Arg Asp Glu Arg
                                                405             410 atc ttc ccc gac ccg gag acg ttc aat ccc gag aga tac ttg aac atg  3324
Ile Phe Pro Asp Pro Glu Thr Phe Asn Pro Glu Arg Tyr Leu Asn Met
            415                 420                 425 gat cca gag acc aag aag aag caa gat cca cgg aac ttc atc ttc gga  3372
Asp Pro Glu Thr Lys Lys Lys Gln Asp Pro Arg Asn Phe Ile Phe Gly
        430                 435                 440 ttc ggt cga ag gtttgtccac gcatgctggc tgcaactgga atctgcaact       3423
Phe Gly Arg Arg
        445 gactgtcatt cgccttag g ctt tgc cct gga aat cat atc gta gat gct tcg 3475
```

```
                    Leu Cys Pro Gly Asn His Ile Val Asp Ala Ser
                                    450                 455 ctg tgg ctg ttg gtc gtt cgc atg atg gct acc ctt gat atc tct acc        3523
Leu Trp Leu Leu Val Val Arg Met Met Ala Thr Leu Asp Ile Ser Thr
        460                 465                 470 ccc gtc gac gag aaa ggc aat gca att gat att gtt ccg gtt ttc gac        3571
Pro Val Asp Glu Lys Gly Asn Ala Ile Asp Ile Val Pro Val Phe Asp
    475                 480                 485 aac cct atc ttc ag gttcgccgc atccgtcccc tggttactct gtactgaatg          3625
Asn Pro Ile Phe Arg
490 tcttttctca tgctag a acg cca aat ccc ttc ccc tgc gat atg cga cca cgt    3678
              Thr Pro Asn Pro Phe Pro Cys Asp Met Arg Pro Arg
                495                 500                 505 tgaaggctgt aaatctcatt cgacaatacg ccgaccctcg cgcctctgca taatcttctg      3738
tcagccatat acaaactacg acctcgctca cagccgcgga ctcttcgaca ctggccttt      3798 cgagcttata tgaccggaat tatcactcta gggatctgtc caaaggtta agcgacgatt      3858 gaattttca gacattttg catctcttcc cacttctagc cttagattta aagttctacg       3918
gggcacagta tcacctccat cttttttctc aattatcctt gttcggtccc ggatggcaca     3978
ttctttatat cagccatggt cactcctttc tctatctcgc tccctacatt tccacccatt     4038
tatcattatg acctgcattc atctcgaata cccacaggat aggacggttc ggcgctttga     4098
ttaaattacg actcgcatct agcgtatact gtacaccttc attaccgtag tcgtcacctt     4158
tcaaccagaa acgcctcgaa acaccgcaca ccgcgtgtac tttcagtgtt aagtggaaat    4218
tcagatcttt ccaacctcgg gctttggatg tgatatttga atctcggaga cgatgaagcg    4278
agcggagact cctttgcgag gtttttggtg ctcgatgctt ctattcccgt tgctgccttt    4338
atcagttcca acttctgcgt ca                                              4360

<210> SEQ ID NO 6
<211> LENGTH: 1521
<212> TYPE: DNA
<213> ORGANISM: Coprinus cinereus
<220> FEATURE:
<221> NAME/KEY: CDS
<222> LOCATION: (1)..(1521)

<400> SEQUENCE: 6 atg aca acg acg agc agt agt atc ttc gct ggt cta gga tgc ctt ctt        48
Met Thr Thr Thr Ser Ser Ser Ile Phe Ala Gly Leu Gly Cys Leu Leu
1               5                   10                  15 gtc gcc tcc atc att tac ttc cgg aag ctt aaa gct aac ccg gca cga        96
Val Ala Ser Ile Ile Tyr Phe Arg Lys Leu Lys Ala Asn Pro Ala Arg
            20                  25                  30 gct cac ctc cct cct ggt ccc aaa ccc att ccc gta ctc ggc aac gtc       144
Ala His Leu Pro Pro Gly Pro Lys Pro Ile Pro Val Leu Gly Asn Val
        35                  40                  45 aaa gac ctt cga gcg aaa gag cta tgg ctg ccg gcg atg gac tgg gcg       192
Lys Asp Leu Arg Ala Lys Glu Leu Trp Leu Pro Ala Met Asp Trp Ala
    50                  55                  60 aag caa tac ggc gat atc acc tac ctt cac gtc ttt gga caa ggt ctc       240
Lys Gln Tyr Gly Asp Ile Thr Tyr Leu His Val Phe Gly Gln Gly Leu
65                  70                  75                  80 aca ttt atc aac tcc ttg gaa tct gca agc gac ttg ctc gag aaa cga       288
Thr Phe Ile Asn Ser Leu Glu Ser Ala Ser Asp Leu Leu Glu Lys Arg
                85                  90                  95 ggc ggc atg tac gcc gac aaa cct cag ttt acc atg gtt tgc gaa ctg       336
```

```
                                                    -continued

Gly Gly Met Tyr Ala Asp Lys Pro Gln Phe Thr Met Val Cys Glu Leu
            100                 105                 110 tgc aac tgt aag aat atg gtt gcc ttt acg ccc tac gga gaa cag tcg        384
Cys Asn Cys Lys Asn Met Val Ala Phe Thr Pro Tyr Gly Glu Gln Ser
            115                 120                 125 aag cga caa cgg cga ttg atg cac aaa gct ttc gcc cct gct cgc atc        432
Lys Arg Gln Arg Arg Leu Met His Lys Ala Phe Ala Pro Ala Arg Ile
        130                 135                 140 ccg gat tat cat ccc tta atg gaa tca tca acc aac ctc ttc ctc cga        480
Pro Asp Tyr His Pro Leu Met Glu Ser Ser Thr Asn Leu Phe Leu Arg
145                 150                 155                 160 aac gtc att gca tcc ccg gcc gat tat atc ggt cac gta cga agg tac        528
Asn Val Ile Ala Ser Pro Ala Asp Tyr Ile Gly His Val Arg Arg Tyr
                165                 170                 175 tct ggt tca ctc acg ctc aac att gtc tat ggg tac gaa gtc act tcc        576
Ser Gly Ser Leu Thr Leu Asn Ile Val Tyr Gly Tyr Glu Val Thr Ser
            180                 185                 190 aac gaa gac gaa tat ctt atg atg gcg gag gag tgt gtc ggt att ctc        624
Asn Glu Asp Glu Tyr Leu Met Met Ala Glu Glu Cys Val Gly Ile Leu
        195                 200                 205 gct aac gaa att gcg agt gct gga ggt gtt tgg gct gtc gat gtc atg        672
Ala Asn Glu Ile Ala Ser Ala Gly Gly Val Trp Ala Val Asp Val Met
    210                 215                 220 cct ttc ctc gct aag atc cct aaa tgg gca gag gga ttg cca gga atg        720
Pro Phe Leu Ala Lys Ile Pro Lys Trp Ala Glu Gly Leu Pro Gly Met
225                 230                 235                 240 agc ttt aaa cgg aag gcg agg aag tgg aag aag atg atg gag gat tgg        768
Ser Phe Lys Arg Lys Ala Arg Lys Trp Lys Lys Met Met Glu Asp Trp
                245                 250                 255 gtt gat gga cca ttc gaa tac gtc aag aac acc atg aaa agc ggc act        816
Val Asp Gly Pro Phe Glu Tyr Val Lys Asn Thr Met Lys Ser Gly Thr
            260                 265                 270 tac aag caa tca ttc tgc tct tcc cta tta gac gat gaa agt atc tcg        864
Tyr Lys Gln Ser Phe Cys Ser Ser Leu Leu Asp Asp Glu Ser Ile Ser
        275                 280                 285 caa acc cag gag cac ttc gaa ttt gac ttg aag tgg acg gct aac tcg        912
Gln Thr Gln Glu His Phe Glu Phe Asp Leu Lys Trp Thr Ala Asn Ser
    290                 295                 300 atg tat gca gcc agc atc gat act acg att acc tca gtc gct cac ttc       960
Met Tyr Ala Ala Ser Ile Asp Thr Thr Ile Thr Ser Val Ala His Phe
305                 310                 315                 320 cta ctt gca atg atg aag cac ccc gaa gtc ttg aag aag gca cag cat      1008
Leu Leu Ala Met Met Lys His Pro Glu Val Leu Lys Lys Ala Gln His
                325                 330                 335 gaa atc gat acc gtt gtc gga caa gat cgc ctc ccc acc ttc agc gac      1056
Glu Ile Asp Thr Val Val Gly Gln Asp Arg Leu Pro Thr Phe Ser Asp
            340                 345                 350 agg aag tct ttg cca tat gtt gaa gcc gtc ctc tcc gag act tgg aga      1104
Arg Lys Ser Leu Pro Tyr Val Glu Ala Val Leu Ser Glu Thr Trp Arg
        355                 360                 365 tgg gct tcc ccc gtc cca ttg agc ttg cct cat aaa ttg act gaa gat      1152
Trp Ala Ser Pro Val Pro Leu Ser Leu Pro His Lys Leu Thr Glu Asp
    370                 375                 380 gac gtg tat cga gga atg tat atc ccg aag ggt tcc ttg atc ttc gcc      1200
Asp Val Tyr Arg Gly Met Tyr Ile Pro Lys Gly Ser Leu Ile Phe Ala
385                 390                 395                 400 aat atc tgg gcg atg aca cga gat gag cgc atc ttc ccc gac ccg gag      1248
Asn Ile Trp Ala Met Thr Arg Asp Glu Arg Ile Phe Pro Asp Pro Glu
                405                 410                 415
```

-continued

```
acg ttc aat ccc gag aga tac ttg aac atg gat cca gag acc aag aag    1296
Thr Phe Asn Pro Glu Arg Tyr Leu Asn Met Asp Pro Glu Thr Lys Lys
            420                 425                 430 aag caa gat cca cgg aac ttc atc ttc gga ttc ggt cga agg ctt tgc    1344
Lys Gln Asp Pro Arg Asn Phe Ile Phe Gly Phe Gly Arg Arg Leu Cys
            435                 440                 445 cct gga aat cat atc gta gat gct tcg ctg tgg ctg ttg gtc gtt cgc    1392
Pro Gly Asn His Ile Val Asp Ala Ser Leu Trp Leu Leu Val Val Arg
        450                 455                 460 atg atg gct acc ctt gat atc tct acc ccc gtc gac gag aaa ggc aat    1440
Met Met Ala Thr Leu Asp Ile Ser Thr Pro Val Asp Glu Lys Gly Asn
465                 470                 475                 480 gca att gat att gtt ccg gtt ttc gac aac cct atc ttc aga acg cca    1488
Ala Ile Asp Ile Val Pro Val Phe Asp Asn Pro Ile Phe Arg Thr Pro
                485                 490                 495 aat ccc ttc ccc tgc gat atg cga cca cgt tga                        1521
Asn Pro Phe Pro Cys Asp Met Arg Pro Arg
            500                 505
```